US00PP35144P2

(12) United States Plant Patent
Chen et al.

(10) Patent No.: US PP35,144 P2
(45) Date of Patent: May 2, 2023

(54) PEACH TREE NAMED 'CARDINAL JOY'

(50) Latin Name: ***Prunus persica* (L.) Batsch.**
Varietal Denomination: Cardinal Joy

(71) Applicant: The United States of America, as represented by the Secretary of Agriculture, Washington, DC (US)

(72) Inventors: Chunxian Chen, Byron, GA (US); William R. Okie, Augusta, GA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 17/881,660

(22) Filed: Aug. 5, 2022

(51) Int. Cl.
*A01H 5/08* (2018.01)
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 6/7463
See application file for complete search history.

*Primary Examiner* — Anne Marie Grunberg
(74) *Attorney, Agent, or Firm* — John D. Fado; Maria Restrepo-Hartwig

(57) ABSTRACT

A new and distinct cultivar of peach tree, denominated 'Cardinal Joy', has firm, melting, semi-freestone fruit with a high coverage of red blush, yellow flesh, normal acidity, rich flavor and pleasant eating quality at maturity. The fruit typically ripen about a week after 'Flavorich' (syn. 'Rich May') and a few days before 'Carored' in mid to late May at Byron, Ga. The tree has self-fertile showy pink flowers and is moderately vigorous and semi-spreading in growth habit. This cultivar has a winter chilling requirement of approximately 850 chill hours, crops well most years, and is suited for high chill areas.

4 Drawing Sheets

Latin name of the genus and species of the plant claimed: 'Cardinal Joy' is a new tree of peach with the Latin name of *Prunus persica* (L.) Batsch.

Cultivar denomination: The new peach tree is denominated 'Cardinal Joy'.

BACKGROUND OF THE NEW PLANT

The present invention relates to a new and distinct peach cultivar designated 'Cardinal Joy', botanically known as *Prunus persica* (L.) Batsch, and tested as BY02P3726 obtained from a hand-pollinated cross between BY93P3635 (an advanced selection, unpatented, the seed parent) and 'Rich Joy' (patented: U.S. Plant Pat. No. 31,081, the pollen parent) yellow peaches. Fruit of 'Cardinal Joy' ripen approximately 28 days before 'BY93P3635' and 54 days earlier than 'Rich Joy'. This new peach tree is adapted to a Southeastern subtropical climate with high chill in winters. Its high chilling requirement (~850 chill hours) and desired early ripening season make it worthy of commercial production trials for the fresh fruit market. Clonal plants were asexually propagated from the original 'Cardinal Joy' tree by grafting on 'Guardian'® peach seedling rootstocks in Byron, Ga. These asexually propagated plants, along with all characteristics of the tree and the fruit, remained true-to-type to the original 'Cardinal Joy' tree. There are no known effects of the standard rootstock on the scion cultivar characteristics.

'Cardinal Joy' produces firm, melting, semi-freestone, yellow-flesh fruit with normal acidity, rich flavor, attractive red skin color (blush) and yellow background, which ripens in mid to late May in Byron, Ga. 'Cardinal Joy' is a promising candidate for commercial success in the early harvest season in that it has a high chilling requirement and crops very well with attractive, rich-Cardinal fruit.

Byron, Ga is under a subtropical climate. Winters are short, mild and with little snow; summers are long, hot and humid. The average January low temperature is about 1.2° Celsius (34.2° Fahrenheit) and the average July high temperature is about 33.2° Celsius (91.8° Fahrenheit). The hours with temperatures below 7.2° Celsius (45.0° Fahrenheit) vary between 600 and 1200 hours per year. There are about 67 rainy days per year. Average annual precipitation (rainfall) is 1182.9 millimeters (46.6 inches) with great monthly and yearly variabilities and frequent thunderstorms in summers.

SUMMARY OF THE INVENTION

The new and distinct cultivar 'Cardinal Joy' peach tree blooms mid to late March, approximately with 'Elberta' (unpatented) peach trees in Byron, Ga. The estimated chilling requirement, based on bloom time, is approximately 850 chill hours. The blooming period and the blooming date are dependent on climatic conditions. The flower anthers are yellow, and leaf glands are reniform, characteristic of many standard peach cultivars.

The first fruit of 'Cardinal Joy' ripen generally in mid to late May (the early season) in Byron, Ga., approximately a week after 'Flavorich' (syn. 'Rich May', patented: U.S. Plant Pat. No. 7,432) and a few days before 'Carored' (unpatented). 'Cardinal Joy' fruit tend to have rich flavor and approximately 90% red skin (more than 'Flavorich' fruit that have ~60%). 'Cardinal Joy' trees are productive and crop reliably. The potential for commercial production of fresh 'Cardinal Joy' fruit is high because it is one reliable higher-chill alternative (~850 chill hours) that ripens during the harvest seasons of 'Flavorich' (~700 chill hours) and 'Carored' (~650 chill hours) that bloom earlier and thus usually incur higher risk of crop loss to spring freeze.

BRIEF DESCRIPTION OF THE PHOTOGRAPHS

The accompanying drawings are color photographs that are taken at Byron, Ga. and as nearly true as it is reasonably possible to make in a color illustration of this type:

FIG. 1 is a color photograph that shows a close view of typical ripening fruit of the new cultivar 'Cardinal Joy'.

FIG. 2 is a color photograph that shows attractive shapes, skin and flesh colors, and semi-freestones of six specimens of 'Cardinal Joy' fruit arranged in four columns: back and suture side view (top and bottom in column 1); stem and blossom end view (2), back-suture longitudinal halves with and without the semi-freestone (3), and equatorial latitudinal halves with and without the semi-freestone (4).

Figure 1:
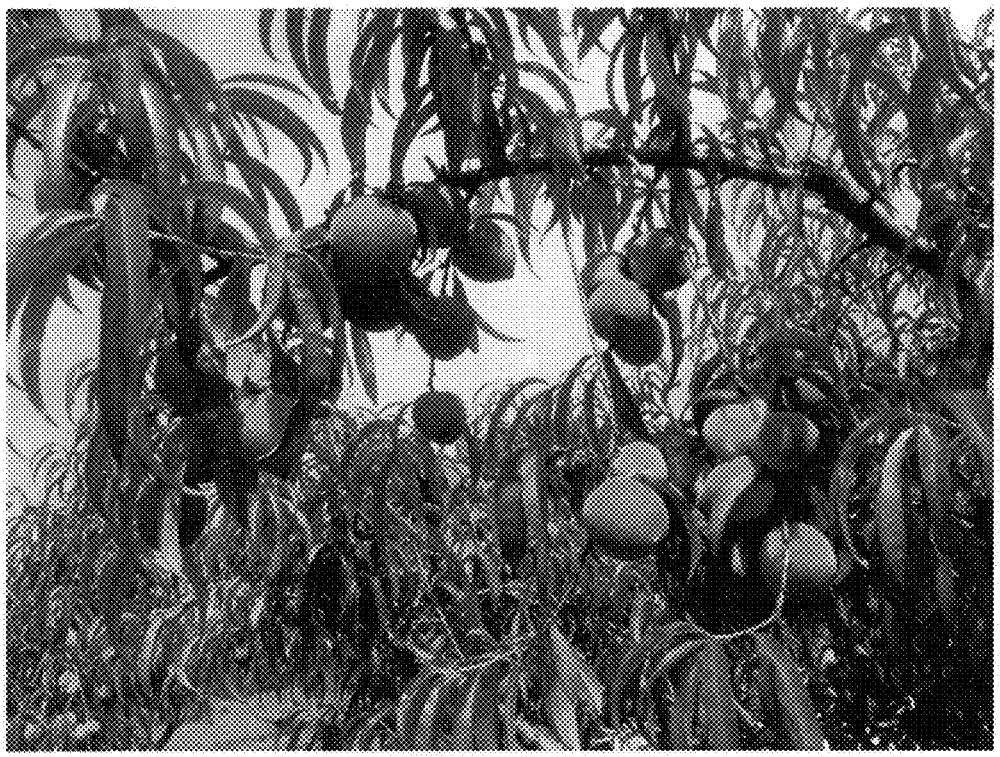
Figure 2:
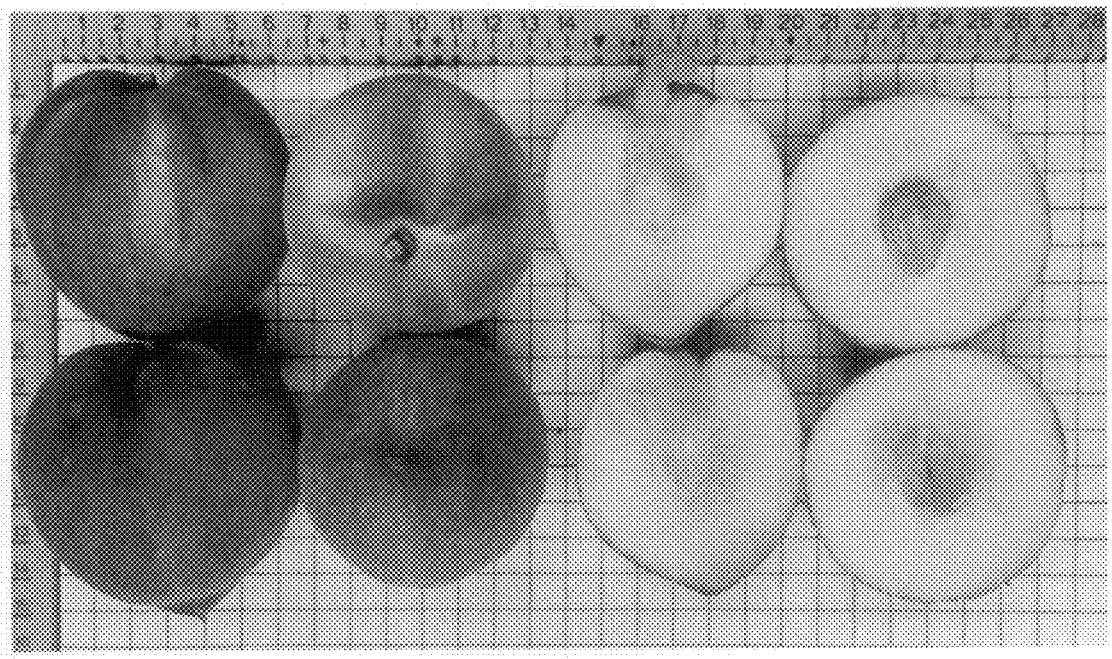
Figure 3:
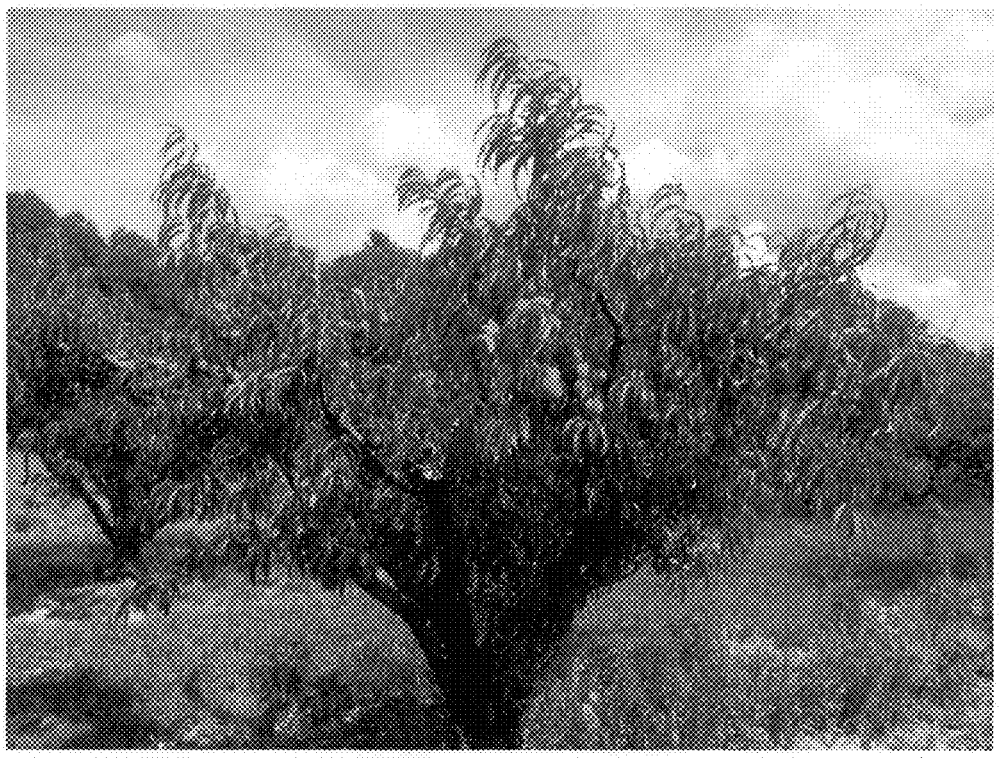
FIG. 3 is a color photograph that shows the typical semi-spreading architecture of a 12-year-old annually pruned tree of the new cultivar 'Cardinal Joy'.
Figure 4:
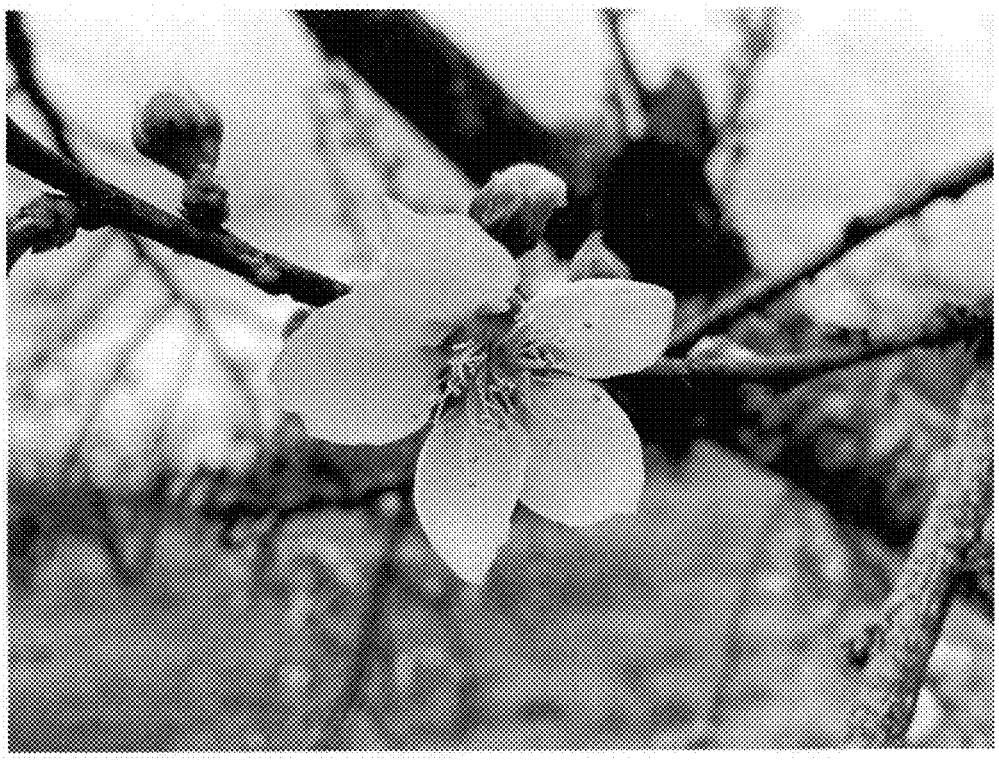
FIG. 4 is a color photograph that shows typical showy flowers of the new cultivar 'Cardinal Joy'.

Due to light, exposure, and other photographical parameters and technologies, the leaves and fruit depicted in these photographs may or may not be accurate when compared to the actual botanical specimen.

DETAILED BOTANICAL DESCRIPTION

The tree, flowers, fruit, and other botanical parts may vary in slight detail due to variations in climatic conditions, cultural practices, development stages, growing seasons, soil types, and tree ages. Referring more specifically to the detailed botanical description of this new and distinct cultivar of yellow-flesh peach tree, the following was observed on 12-year-old trees of the cultivar grafted on 'Guardian'® rootstock under the ecological conditions prevailing at the orchards located at the town of Byron, Ga., USA. All major color code designations are by reference to The Great Britain Royal Horticultural Society (R.H.S.) Colour Chart (Fourth Edition).

Tree:

*Bearer*.—Regular. The fruit must be thinned to obtain large fruit size and avoid limb breakage.

*Canopy density*.—Considered dense. Pruning is required to open the tree center to promote sunlight entrance for enhancing fruit color and sugar.

*Estimated chilling requirement*.—Approximately 850 chill hours based on time of bloom and leafing in relation to standard cultivars.

*Vegetative bud break time*.—Mid-late March in Byron, Ga., approximately 1 week after bloom depending on winter chilling and amount of warm weather.

*Form*.—Semi-spreading, but easily pruned to vase shape.

*Hardiness*.—Hardy with respect to typical GA winters.

*Productivity*.—Very productive and regular, every year. Fruit set is reduced by thinning to develop the remaining fruit into desired market size. The fruit number varies with the prevailing climatic conditions and cultural practices.

*Size*.—Generally considered large when trained to an open vase form. The height and width of 12-year-old annually pruned tree are 3.2 meters and 4.5 meters, respectively, including current season shoots.

*Spread*.—Grown to a vase shape with summer and winter pruning to keep the tree open to get strong fruiting wood in the lower center.

*Vigor*.—Considered moderately vigorous. Approximately 0.9 to 1.2 meters in height and width of annual growth occurs in the orchards at Byron, Ga.

Trunk:

*Bark color*.—RHS Greyed-Green Group 197D. Bark crack's color is RHS Brown Group 200C.

*Lenticel color*.—RHS Brown Group 200A both outside and inside.

*Lenticel count and size*.—Low number, on average approximately 0.5 per square cm of surface area of trunk; and the average lenticel length and width of lenticels are approximately 15.1 millimeters and 3.2 millimeters, respectively.

*Size*.—Approximately 19.7 cm in diameter at a height of approximately 30.0 cm on the 12-year-old trees at Byron, Ga.

Branches:

*Current season new shoots*.—The color is RHS Yellow-Green Group 145B at the upper part (sunny side) of the shoots and RHS Yellow-Green Group 145A at the lower part (shady side) of the shoots.

*Current season mature fruiting limbs*.—The color is RHS Grey-White Group 156A at the upper part (sunny side) of the shoots and RHS Greyed-Green Group 197A at the lower part (shady side) of the shoots. The diameter is from 6.9 to 11.9 millimeters with an average 9.2 millimeters. Tree growth and structure permits easier and faster winter pruning.

*Crotch angles*.—Moderate to wide angles within the normal range of standard cultivars for a semi-spreading tree after proper summer and winter pruning.

*Internode length*.—Approximately 2.2 to 2.9 centimeters with the average of 2.6 centimeters.

*Surface texture*.—Relatively smooth, numerous lenticels but smaller size than found on trunk and old scaffolds. Roughness increases with age.

Leaves:

*Size*.—Considered medium to large for the species.

*Length*.—Approximately 150.0 to 172.0 millimeters with the average of 158.8 millimeters, not including the petiole.

*Width*.—Approximately 31.0 to 38.0 millimeters with the average of 34.5 millimeters.

*Thickness*.—Regular and average for commercial cultivars, approximately 0.15 to 0.22 millimeters with the average of 0.19 millimeter, not noticeably unusual.

*Form*.—Lanceolate.

*Apex*.—Acute.

*Margin*.—Serrulate.

*Base*.—Acute or cuneate.

*Surface*.—Upper, glabrous; Lower, medium to large veins that are pinnately netted.

*Color*.—Regular green, slightly different in seasons. In early shoot growth, upper leaf surface is RHS Green Group 137B and lower leaf surface RHS Yellow-Green Group 146B. In late season, upper leaf surface is RHS Green Group 137C and lower surface is RHS Yellow-Green Group 146B. Leaf vein is RHS Yellow-Green Group 145D.

*Glands*.—Reniform. Usually 1-2 on lower leaf blade and 1-4 on petioles. The length is 0.8 to 1.6 millimeters with an average of 1.2 millimeters and width 0.3 to 0.6 millimeters with an average of 0.5 millimeters. Color is RHS Green Group 138D.

*Petiole*.—Approximately 8.4 to 12.5 millimeters length, approximately 1.4 to 2.0 millimeters diameter. Color is RHS Yellow-Green Group 146D.

*Stipules*.—Medium, equal to most commercial peach cultivars, visible on younger leaves, usually about 2 per leaf, and abscising just before leaf becomes full size in summer growth. Color at full size is RHS Red Group 46A before abscising.

*Leaf blade incisions*.—Serrulate.

*Arrangement*.—Alternate.

*Cross-section shape*.—Leaf blade forms a vee of about 130 degrees.

Flowers:

*Flower buds*.—The form of flowers buds changes as blooming approaches, with variable dimensions. They are conic at pre-floral stage and approximately 4.6 to 6.8 millimeters long and 2.2 to 3.3 millimeters wide. The bud color in mid-winter is RHS Greyed-Green Group 195B. The abundance is very high due to shorter than average internode length. Most buds set fruit in absence of spring frosts and show little evidence of bud drop.

*Hardiness*.—Hardy with respect to GA winters.

*Date of bloom*.—Mid-late March depending on winter chilling and amount of warm weather.

*Blooming time*.—Considered medium-late in bloom relative to other commercial peaches in central GA. Typically blooms with 'Elberta'.

*Duration of bloom*.—Approximately 6 to 14 days. This characteristic varies significantly with amount of winter chilling as well as temperatures during bloom.

*Bloom quantity*.—Generally abundant, with a good distribution.

*Flower bud frequency*.—Generally one flower bud per node, but occasionally two.

*Fragrance*.—Undetectable or faint floral scent.

*Type*.—Showy.

*Shape*.—Rosette.

*Fertility*.—Self-fertile.

*Size*.—Approximately 39.8 to 45.6 millimeters in diameter at full bloom, with the average of 42.6 millimeters.

*Petal*.—Size: Generally considered large. Length: approximately 16.6 to 22.4 millimeters with the average of 18.7 millimeters. Width: approximately 11.2 to 15.5 millimeters with the average of 13.3 millimeters. Form: generally round-shaped. Count: almost always five. Arrangement: usually free, sometimes touching. Texture: smooth, soft and glabrous. Color: RHS Red-Purple Group 65A in the upper surface and RHS Red-Purple Group 63C in the lower surface. Margins: Generally slightly undulating. Apex: generally round and curved- shaped.

*Pedicel*.—Length: approximately 5.2 to 7.5 millimeters with the average of 6.3 millimeters. Diameter: approximately 2.7 to 4.2 millimeters with the average of 3.6 millimeters.

*Calyx cup*.—Diameter: approximately 14.6 to 18.7 millimeters with the average of 17.0 millimeters. Color: RHS Yellow-Green Group 150C at the interior surface and Red-Purple Group 59B at the exterior surface.

*Sepals*.—Number: generally five sepals. Length: approximately 6.1 to 7.4 millimeters with the average of 6.6 millimeters. Width: approximately 4.2 to 5.0 millimeters with the average of 4.5 millimeters. Color: RHS Greyed-Green 191A.

*Stamen number*.—Approximately 33 to 46 stamens per flower with the average of 38.5.

*Anthers*.—Color: RHS Greyed-Orange 163A at opening. Anthers project above petals.

*Pollens*.—Generally abundant and approximately RHS Greyed-Orange Group 163A.

*Filaments*.—Length at opening: approximately 11.1 to 16.0 millimeters with the average of 13.5 millimeters. Color: RHS Red-Purple Group 72B.

*Pistil*.—Number: Usually one. Length: approximately 7.3 to 11.4 millimeters with the average of 9.5 millimeters. Color: RHS Yellow-Green Group 150C (Pistil tip color is RHS Yellow-Green Group 144B). Stigma slightly below anthers.

Fruit:

*Maturity when described*.—Tree ripe, May 19, 2019 at Byron, Ga., and firm in ripe conditions.

*Date of harvest*.—Varies slightly with the prevailing climatic conditions. The picking starts first on May 19, 2019.

*Size*.—Generally uniform medium to large size. Weight: approximately 131.6 to 160.2 grams with the average of 144.9 grams. Equatorial diameter: approximately 63.1 to 67.7 millimeters with the average of 65.2 millimeters. Polar diameter (from stem to distal end) in the suture-back circle is approximately 64.8 to 69.1 millimeters with the average of 66.9 millimeters; and that in the cheek-cheek circle is approximately 65.1 to 70.7 millimeters with the average of 67.1 millimeters. This characteristic highly depends on fruit number per tree, climate, soil type, cultural practices and environmental conditions, and therefore is not particularly distinctive of the cultivar.

*Peduncle*.—Length: approximately 4.3 to 6.3 millimeters with the average of 4.9 millimeters. Width: approximately 2.2 to 3.3 millimeters with the average of 2.8 millimeters. Color: RHS Green Group 139D.

*Longitudinal section form*.—Generally round to ovate with a pronounced tip in some years.

*Transverse section through diameter*.—Usually round.

*Suture*.—Smooth or slightly indented from stem to tip.

*Ventral surface*.—Generally rounded.

*Shape of fruit base*.—Slightly Truncate.

*Apex*.—Generally round to ovate, sometimes with slightly pronounced tips.

*Crater at stem attachment*.—Depth in the suture-back orientation is approximately 16.6 to 26.3 millimeters with the average of 22.5 millimeters; and depth in the cheek-cheek orientation is approximately 10.4 to 19.1 millimeters with the average of 15.4 millimeters. Width at top: approximately 18.0 to 27.0 millimeters with the average of 23.1 millimeters at top. Width at bottom (pedicel attachment): approximately 3.9 to 6.1 millimeters with the average of 5.1 millimeters.

*Skin*.—Thickness: generally medium in comparison to commercial peach cultivars. Texture: generally typical of commercial peach cultivars. Tenacity: Tenacious. Color: RHS Grey-Purple 187B, approximately 80% to 90% of skin. Fruit exposed to sunlight likely have a higher degree of enhanced skin color. Ground color: RHS Yellow 5C. Tendency to crack: Not observed. Taste: No astringency observed. Epidermis: Typical short pubescence.

*Flesh*.—Ripening: evenly within each fruit. Texture: smooth and firm when fully ripe. Fibers: very fine, small, tender, and abundant. Aroma: typical of commercial peach cultivars. Eating quality: rich flavor with typical acidity for fresh consumption. Soluble solid content: 9.4 to 13.7° Brix, with an average of 11.17 of ten fruits harvested on May 20, 2019. pH values: 3.1 to 3.5, with an average of 3.32 of ten fruits harvested on May 20, 2019. Juice: moderately abundant. Color: RHS Yellow-Orange 15A. Color of red flecks within flesh: RHS Orange-Red 31A. Color of flesh at the stone: RHS Yellow-Orange 15A. Browning by oxidation: none observed on tree ripe fruit beginning to soften.

Stone:

*Type*.—Semi-freestone.

*Size*.—Generally medium large. The stone size varies upon the tree vigor, crop load and prevailing growing conditions. Length: approximately 31.4 to 39.2 millimeters with the average of 34.6 millimeters. Width: approximately 21.1 to 26.1 millimeters with the average of 23.7 millimeters. Diameter: approximately 15.9 to 19.4 millimeters with the average of 17.5 millimeters.

*Wall thickness*.—Approximately 5.3 to 6.1 millimeters with the average of 5.6 millimeters.

*Color*.—RHS Orange 26D when flesh is freshly cut.

*Form*.—Oblong.

*Base*.—Acute.

*Apex*.—Acute.

*Sides*.—Unequal.

*Surface*.—Generally furrowed toward ventral edge and lighted pitted from base to apex.

*Tendency to split*.—None observed.

*Kernel*.—Not viable if stratified upon removal from fruit at harvest. Taste: bitter. Size: Considered medium large. Length: approximately 16.0 to 19.3 millimeters with the average of 17.3 millimeters. Width: approximately 9.1 to 11.6 millimeters with the average of 10.7 millimeters. Thickness: approximately 4.2 to 5.6 millimeters with the average of 5.0 millimeters. Form: generally ovate with acute tip and ovate base. Color: RHS Yellow-White 158A.

Use of the fruit: Fresh, dessert.

Keeping quality: Excellent after about two weeks at approximately 2 to 8 degrees Celsius and with little bruising or scarring appearing on skin.

Shipping quality: Considered good. The fruit showed little bruising of the flesh or skin damage after normal harvesting and packing procedures. The fruit retained firmness and showed no internal breakdown of flesh or appreciable loss of eating quality under refrigeration at approximately 2 to 8 degrees Celsius indicates fruit should be highly acceptable for shipping.

Resistance to disease: High resistance to bacterial spot incited by *Xanthomonas campestris* pv. *pruni*. No unusual resistance or susceptibility to insects and diseases was noted.

We claim:

1. A new and distinct cultivar of peach tree named 'Cardinal Joy' as illustrated and described, characterized by a high chilling requirement, an early maturity, and attractive ripe fruit with abundant red blush, vivid yellow ground color, semi-freestone, melting texture, yellow flesh, normal acidity, rich flavor, and pleasant eating quality.

* * * * *